United States Patent [19]
Molko

[11] Patent Number: 6,083,206

[45] Date of Patent: Jul. 4, 2000

[54] INTRAVENOUS INFUSION FLOW RATE MONITORING DEVICE

[75] Inventor: Albert Molko, Sandweiler, Luxembourg

[73] Assignee: Midex Marketing Limited, Dublin, II, Ireland

[21] Appl. No.: 08/849,563

[22] PCT Filed: Nov. 30, 1995

[86] PCT No.: PCT/EP95/04722

§ 371 Date: Sep. 28, 1997

§ 102(e) Date: Sep. 28, 1997

[87] PCT Pub. No.: WO96/17637

PCT Pub. Date: Jun. 13, 1996

[30] Foreign Application Priority Data

Dec. 7, 1994 [LU] Luxembourg ............... 88565

[51] Int. Cl.⁷ .................................................. A61M 5/00
[52] U.S. Cl. ......................................................... 604/253
[58] Field of Search ................................ 604/65–67, 253

[56] References Cited

U.S. PATENT DOCUMENTS 4,784,643  11/1988  Siretchi et al. ...................... 604/122

*Primary Examiner*—Corrine McDermott
*Attorney, Agent, or Firm*—Cantor Colburn LLP

[57] ABSTRACT

An infusion monitoring device including a programming console with a data input unit for inputting infusion parameters, a calculating unit for preconditioning the parameters, and an output interface for said parameters. The programming console may be used to program a large number of self-contained monitoring units each having a sensor combined with a drop-counting ampoule for sensing the presence or absence of the drop. Each monitoring unit has a housing for a timing and counting unit, a display unit, an alarm unit, a self-contained power supply, and input interface for receiving parameters preconditioned in the programming console, a memory unit for storing the parameters, and a separate calculating unit for controlling the counting/timing, in the display and the alarms.

23 Claims, 8 Drawing Sheets

INTRAVENOUS INFUSION FLOW RATE MONITORING DEVICE

The present invention relates to a device for monitoring the flow rate of an intravenous infusion.

BACKGROUND OF THE INVENTION

Many medicinal substances are administered by intravenous infusion. The toxicity, the requirements as to regularity in the timing of the doses and the physical condition of the patient mean that it is desirable, even essential, to monitor the flow rate of an intravenous infusion.

Infusion by gravity, with manual adjustment of the flow rate by progressive squeezing of the infusion tubing and visual monitoring of the flow rate using a drip cylinder is still the most commonly used infusion method today. It is obvious that the operation of adjusting the flow rate is far from being precise. The nurse must first calculate, in terms of the desired duration of the infusion and the number of drops per unit volume (which depends on the liquid infused and the drip cylinder being used), the time interval between two drops. Then she has to adjust the flow rate by squeezing the infusion tubing while timing the drops in the drip cylinder using a watch. During the whole period of the infusion, she must regularly return to carry out a visual check of the remaining volume and the flow rate of the drops in the drip cylinder, in order to decide subjectively whether the progress of the infusion is roughly acceptable. If she suspects too slow or too fast a rate, she adjusts the flow rate largely by using her own intuition rather than by a recalculation or by retiming the drops.

If there is a desire for greater precision in the adjustment of the flow rate and for assurance that the infusion flow rate is adhered to for the whole duration of the infusion, infusion devices with dosing pumps (also called peristaltic pumps) designed to deliver an almost constant flow rate must be available. However, such devices unfortunately have drawbacks limiting their use. First, the consumption of electrical power by dosing pumps is far from being negligible. When the power is supplied by batteries, the autonomy of these devices is restricted as a result. Their appreciable weight and bulk mean that these devices can rarely be used for other than bedridden patients. Intravenous infusion devices with dosing pumps also entail the use of special tubing (flexible tubes made of silicone). The cost of such special tubing is much greater than that of standard tubing, and its supply complicates the handling of consumable equipment. The use of a dosing pump also means that the delivery pressure has to be monitored. This pressure depends on the back pressure at the point of injection and is therefore a parameter very sensitive to the smallest anomalies. It should also be noted that the very measurement of the delivery pressure is problematic. In effect, because the tubing must remain sterile, the pressure sensors can only be outside the tubing. Now, it is not obvious how to measure an excess pressure through plastic tubing.

Intravenous infusion devices with dosing pumps on the market today are complex automatic items equipped with sophisticated control and adjustment systems, which are often the source of untimely alarms. In these sophisticated control and adjustment systems, it is possible to incorporate a device for controlling the infusion flow rate. Such a flow rate control device comprises an electro-optical sensor of the optical barrier type, which is combined with a drip cylinder to detect the presence or absence of a drop. The signal from the sensor is processed in a counting and timing unit. An ALU (arithmetic and logic unit) monitors the flow rate of the drops in order to trigger an acoustic and/or visual alarm and/or to intervene in the system for adjusting the dosing pump when the flow rate of drops shows a positive or negative deviation from a preset value.

Such a flow rate monitoring device is described, for example, in the document EP-A-0441323. In order to increase the sensitivity of the detection, this document proposes to replace the photodiode by a kind of miniature camera for detecting an image of the drop. It is obvious that such a method does not reduce either the price of the device, or its bulk, or its electrical power consumption.

It would also be of interest to use devices for controlling the infusion flow rate to monitor infusions by gravity. Now, although the price of the flow rate control device is only a minor factor in the case of complex and expensive automatic infusion controllers, this is not so if there is a desire for the systematic use of an autonomous flow rate monitoring device for monitoring infusion by gravity. Such a flow rate monitoring apparatus should be cheap (in view of the large number of appliances required in a hospital), be very compact and consume little power (so as not to restrict the mobility of a patient who is not bedridden), be very convenient to use (so as to guarantee its acceptance by medical staff) and guarantee a high degree of safety in use.

This complex problem, which at first sight requires the solution of completely contradictory problems, finds a simple solution in a device according to the invention.

SUMMARY OF THE INVENTION

According to the present invention, a device for monitoring infusions comprises two types of apparatus, physically independent but functionally related, namely an autonomous and independent programming console and an autonomous and independent monitoring unit.

The programming console comprises:
  a data input unit suitable for entering the characteristic parameters of the infusion;
  its own ALU (arithmetic and logic unit) suitable for preconditioning the characteristic parameters of the infusion entered into the parametric data input unit, and
  an output interface suitable for converting these preconditioned parameters into signals capable of being transmitted over a distance.

Such a programming console can be used to program a large number of autonomous monitoring units, each of which then comprises:
  a sensor suitable for being combined with a drip cylinder to detect the presence or absence of a drop;
  and a cabinet containing the following functional units:
    a unit for timing and counting the drops detected by the said sensor;
    a memory unit for storing the characteristic parameters of the infusion;
    a display unit;
    an acoustic and/or visual alarm unit;
    an ALU capable of using a computer algorithm, involving as parameters a signal from the timing and counting unit and the characteristic parameters of the infusion stored in the memory unit, in order to trigger an acoustic and/or visual alarm;
    an input interface capable of reconstituting the said preconditioned parameters so that they can be loaded into the said memory unit for use by the said first ALU; and an autonomous electrical power supply for the sensor and all those functional units incorporated in the common cabinet.

According to the present invention, a given infusion is associated with an autonomous monitoring unit which has been preprogrammed using the programming console. As a result of this, a hospital can make do with the acquisition of only one programming unit for a large number of monitoring units, which of course appreciably reduces the investment costs involved in ensuring, for example, a systematic monitoring of all the infusions carried out.

The physical separation of the monitoring function and the programming function also has an advantage as regards organization and safety. The autonomous monitoring units can be programmed only by the person with access to the programming console. As a result, access to the programming of the monitoring units can be restricted to staff with the necessary expertise. A person with no access to the programming console cannot change the parameters of an infusion. The responsibility as regards the programming of the monitoring parameters is thus clearly delimited.

The incorporation of the data input unit into an independent programming console makes it possible to design this data input unit in a very user-friendly manner. In effect, the available space, the weight and the electrical power consumption are constraints of a secondary order for the design of the programming console, but are constraints of a first order for the design of a compact and autonomous monitoring unit. Moreover, the price of a programming unit can be spread over a large number of autonomous monitoring units, making it possible to choose an optimum solution from the viewpoint of data acquisition for the infusion, without being obliged to pay too much attention to the cost of this solution.

The programming console has its own ALU, enabling the input data to be preconditioned with a view to their final use in the monitoring unit. This technique of preconditioning input parameters in the programming console reduces the number of operations to be carried out by the ALU of the monitoring unit and hence economises on the electrical energy used by this autonomous monitoring unit.

As regards the autonomous monitoring unit, this may be designed very compactly, since a bulky user-friendly data input unit does not need to be incorporated in the cabinet for the autonomous monitoring unit. Being compact and electrically autonomous, it does not hinder the mobility of the patient.

The data input unit with advantage comprises means for directly entering the volume of the infusion and means for directly entering the duration of the infusion. Thus, there is no possibility of making a mistake during the conversion of these two basic characteristics into a derived quantity, for example the number of drops per minute. This conversion is then carried out automatically by one of the two ALUs, preferably beforehand by the ALU in the programming console.

The data input unit also comprises with advantage means for entering a margin of tolerance. This margin of tolerance is then incorporated in the computer algorithm of the monitoring unit in order to fix a bandwidth around the theoretically required flow rate within which there is no triggering of an alarm. This margin of tolerance enables alarms to be avoided when the deviations detected have no harmful consequences on the overall infusion process. The means for entering a margin of tolerance for the infusion rate preferably comprise means for entering separate margins of tolerance for negative deviations (too slow a rate) and positive deviations (too fast a rate). Depending on the type of infusion or the condition of the patient, it may in fact be recommended that a narrower margin of tolerance be fixed for a negative deviation than for a positive deviation, or vice versa. It will be appreciated that programmable margins of tolerance allow a flexible approach to the monitoring of an infusion which avoids pointless alarms. No attempt is made to maintain a theoretical volume flow rate at any price, rarely necessary in practice, but momentary or overall deviations are allowed within a range of error defined in terms of the type of infusion and condition of the patient.

The parameters used to calibrate the autonomous monitoring unit are also entered with advantage through the intermediary of the data input unit. These parameters used for calibration characterise, for example, the nature of the infusion liquid and the type of drip cylinder used. They make it possible for one of the ALUs, preferably that of the programming console, to calculate the number of drops per unit volume. It is, however, also possible to enter the number of drops per unit volume directly as a calibration parameter.

A user-friendly data input unit, completely acceptable to the medical staff, preferably comprises a keyboard with keys, each of which is dedicated to a commonly used value of a characteristic parameter of the infusion. It is very simple to use this type of keyboard and the risk of mistakes is reduced to a minimum.

In order to give the user a means to control the allocation of the programmed autonomous monitoring unit to a given infusion, the alphanumeric display unit makes it possible to display characteristic parameters of the infusion deduced directly from parameters loaded into the memory unit of the autonomous monitoring unit. These characteristic parameters, preferably displayed in the form of a status bar, preferably comprise the volume of the infusion and the duration of the infusion.

In a preferred embodiment, the alphanumeric display unit displays, preferably graphically in the form of a linear scale, the relative positive or negative difference between the number of drops detected over a moving interval of observation t1 and the number of drops that there should have been during the said interval t1 in the case of a uniform distribution of drops over the total duration initially planned for the infusion. On this same scale, it is then possible to indicate the positive and negative margins of tolerance. These relative values can be displayed in percentage terms, which avoids their being referred to values corresponding to a zero difference.

In order to enable a correction to be made easily to the deviations occurring during the duration of the infusion, the first ALU calculates, in real time, an optimum number of drops defined as follows:

$$\frac{(\sum \text{drops yet to pass}) - (\sum \text{drops already passed})}{(\text{planned total duration of infusion}) - (\text{duration already elapsed})}$$

all this being multiplied by the duration t1 of the moving observation interval. This optimum value can then be graphically displayed on the said linear scale. If there is a need to correct a deviation, it is sufficient to vary the flow rate so as to make a moving reference giving the detected number of drops correspond on the linear scale to a moving reference giving the optimum number of drops.

The sensor connected to the autonomous monitoring unit preferably comprises a source of infra-red radiation functioning in pulsed mode and an optical receiver activated in synchronous mode. The emission/reception in pulsed mode enables the signal/noise ratio (S/N) to be improved, enables the system to be made less sensitive to artificial light (50 or 60 Hz) and at the same time enables the power consumption by the sensor to be limited. In effect, instead of distributing the energy uniformly in time, it is concentrated in the high amplitude peaks of the emission. Moreover, the receiver is activated only at the moment when a light signal is emitted.

The optical receiver with advantage comprises several photodiodes which are connected electrically in series and which are distributed in an angular sector opposite the said source of infra-red radiation. The receiver is an inexpensive unit which is able to detect not only the drops passing in a region close to the central axis of the ampoule but also those passing at a certain distance from this axis when the drip cylinder is inclined. Moreover, this detector is very sensitive to variations in light intensity which concern only a very small fraction of the total photosensitive surface.

In order to couple the input interface of the monitoring unit temporarily to the said interface of the programming console output, an optical coupler is used with advantage. This is a cheap method of coupling which is reliable in a hospital environment increasingly polluted by stray electromagnetic waves.

In order to allow an easy initial adjustment of the infusion flow rate, means of switching are with advantage added to the autonomous monitoring unit in order to switch from a "monitoring/alarm" functioning mode to an "adjustment of flow rate" functioning mode. In the latter functioning mode, audible alarms are out of action and an acoustic unit advantageously produces an acoustic signal for each drop detected. The nurse thus has available an efficient instrument, completely pre-programmed, to carry out the initial adjustment of an infusion by gravity. Calculations of the number of drops and the manual timing of drops are no longer required. As a result, it is impossible to make a mistake over the adjustment of the flow rate.

BRIEF DESCRIPTION OF THE DRAWING

Additional characteristics and advantages of the present invention can be deduced from the detailed description of the attached figures, which represent examples of preferred embodiments of a device according to the invention. In particular.

DETAILED DESCRIPTION OF THE PREFERRED EMBODIMENT

Figure 1:
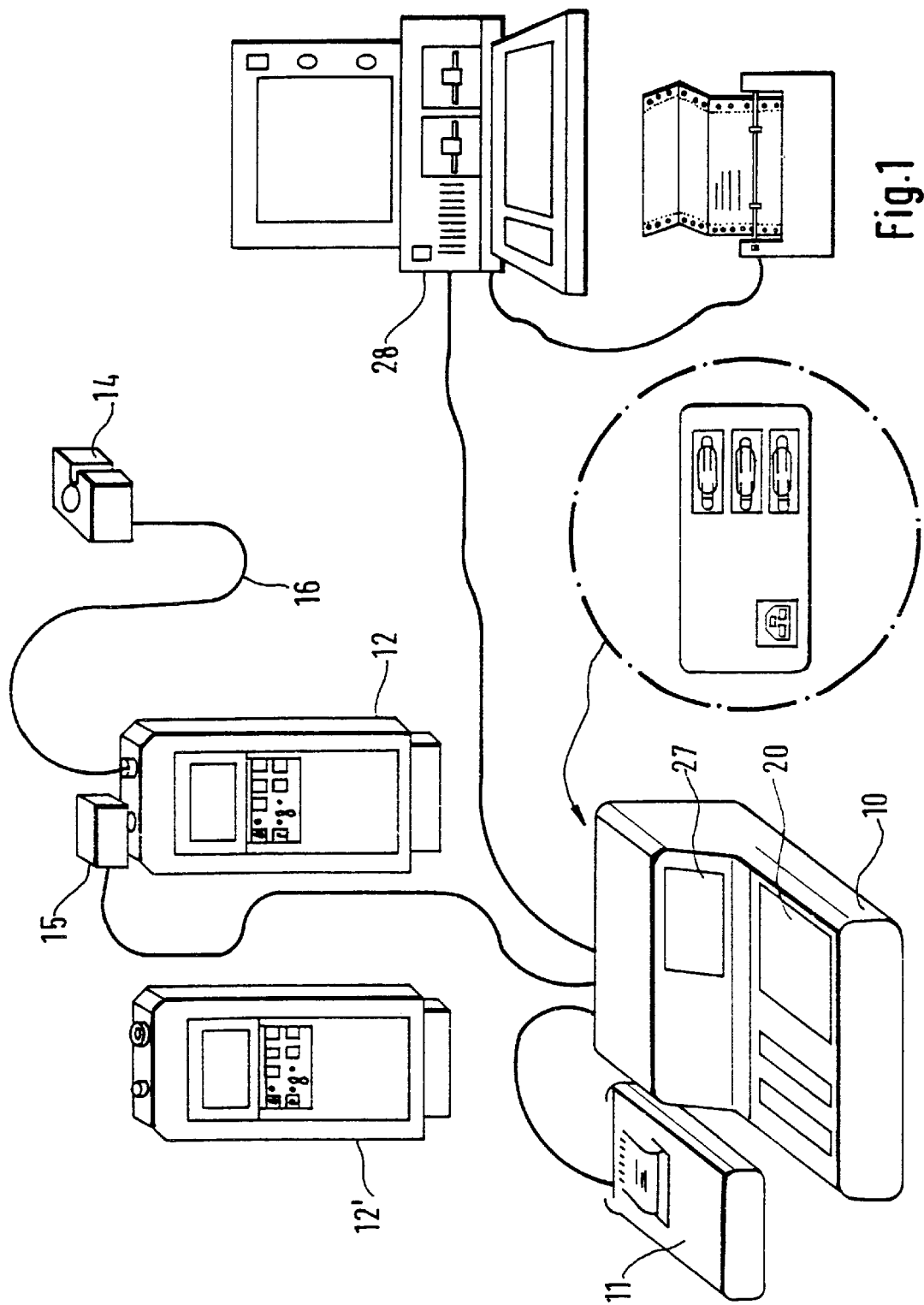
FIG. 1 represents an overall view of an infusion monitoring system according to the invention, comprising an independent programming console with printer, optionally connected to a computer, and autonomous monitoring units, each fitted with a drip sensor.

FIG. 1 shows the various components of a device according to the invention. The principal components are a programming console 10, at least one autonomous monitoring unit 12, 12' and a drip sensor 14.

Connected by a cable 16 to each of these autonomous monitoring units 12, 12' is a drip sensor 14 which can be mounted on a drip cylinder (not represented) of the standard type used for infusion by gravity. An optical coupler 15 is used to couple each of the autonomous monitoring units 12, 12' temporarily to the programming console.

The programming console, the autonomous monitoring unit and the drip sensor will now be studied in detail.

Figure 2:
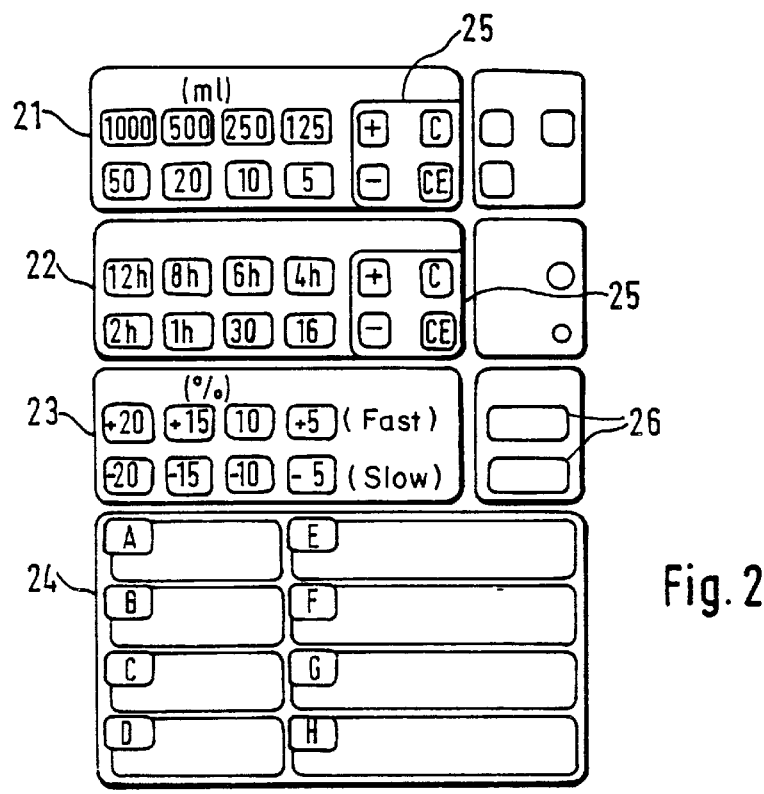
FIG. 2 represents the keyboard of the independent programming console.

1) The programming console:

Reference is made simultaneously to FIGS. 1 and 2, the latter representing the keyboard of a programming console according to the invention.

It will be recalled that the function of the programming console 10 is to program the autonomous monitoring units 12, 12', in other words to load the characteristic parameters of a given infusion —such as the volume of infusion, the duration of infusion, the volume of a drop —into the autonomous monitoring units. In order to allow medical staff to enter these parameters without difficulty and in a user-friendly environment into the programming console 10, the latter advantageously incorporates a keyboard 20 as represented in FIG. 2. This keyboard 20 has a separate block of keys 21, 22, 23, 24 for each type of parameter to be entered. The reference number 21 denotes the block of keys used to enter the volume of the infusion. It can be seen that each key is allocated a volume commonly used for an infusion by gravity, for example: 1000 ml, 500 ml, 250 ml, 125 ml, 50 ml, 20 ml, 10 ml and 5 ml. The reference number 22 denotes a similar block to enter the duration of the infusion. This block 22 comprises individual keys for entering the most commonly used durations for an infusion. The reference number 23 denotes a similar block to enter the margins of error, for example: 20%, 10%, 5% and 2% too fast or too slow by comparison with the theoretical flow rate. The reference number 24 denotes a similar block to enter the parameters for calibrating the device, namely either the type of infusion liquid used and the type of drip cylinder used or directly the number of drops per ml.

Function keys 25 make it possible to add or subtract values for each type of parameter and to correct the input values, to confirm the value of an unusual parameter or of a combination departing from a safety standard, to choose combinations of parameters or calibration (for example, the number of drops per unit volume). Lastly, a combination of two keys 26 enables the input parameters to be validated and to be sent to the autonomous monitoring unit 12.

The console 10 comprises a means of display 27, for example a liquid crystal screen. This screen 27 displays the combinations of input values and warning messages in case of any programming anomaly. The console 10 can be connected to a computer 28, using for example a series-type connector, in order to communicate and receive information about a prescription or clinical information about the patient (for example: a cardiac insufficiency, which imposes a limit on the flow rate and the upper margin of error in order to avoid a volume overload capable of inducing a pulmonary oedema).

A printer 11, which prints a summary of the programmed parameters, may also be connected to the control console 10. This summary, which carries the identification number of the autonomous monitoring unit 12 just programmed, will be introduced into a display window on the autonomous monitoring unit 12, this being done in order to avoid accidental switching between differently programmed autonomous monitoring units 12, 12'.

Figure 7:
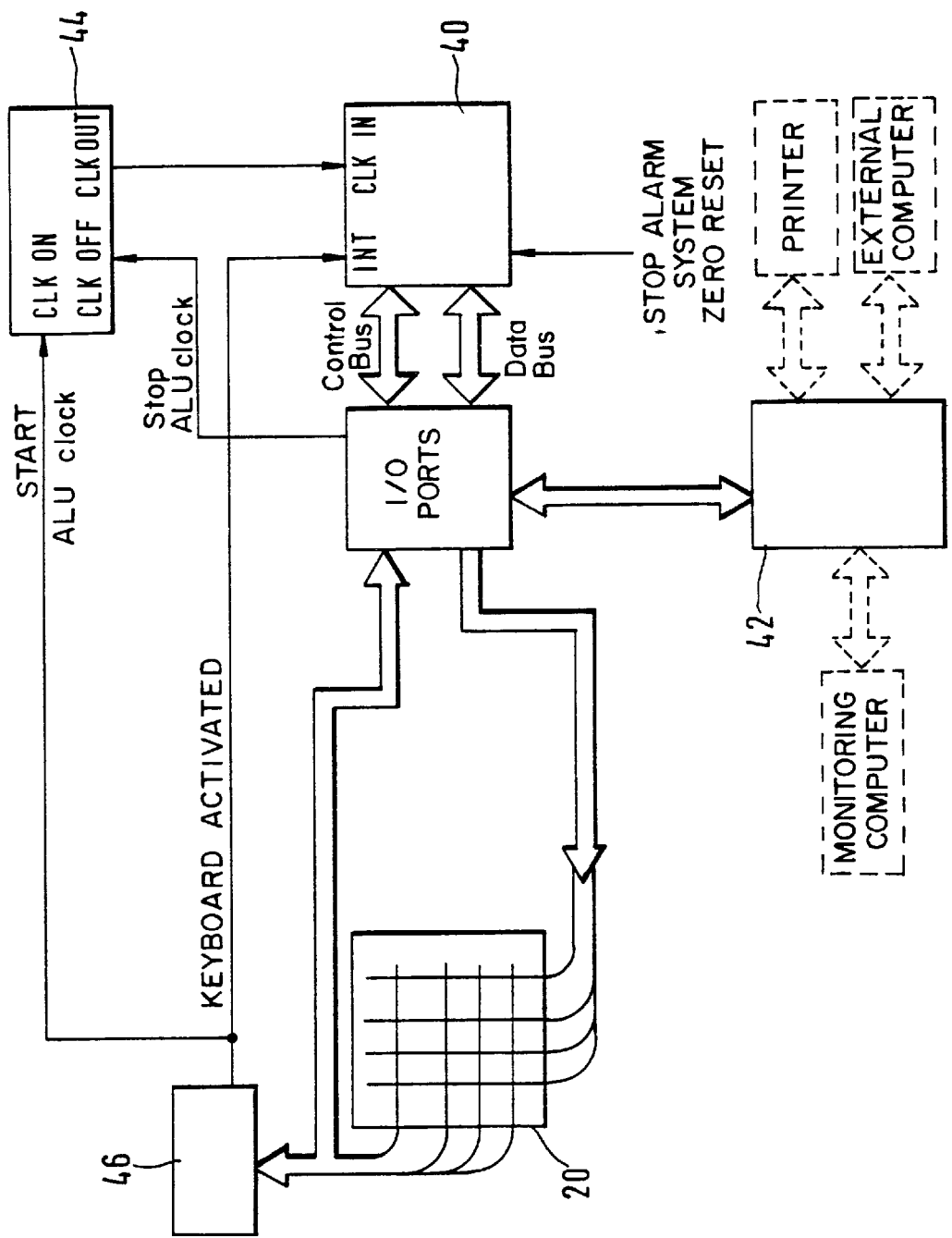
FIG. 7 is a functional block diagram of a programming console.

The functioning and the internal structure of the programming console 10 will be described briefly with the help of FIG. 7. Each rectangle represents a different functional unit. It is obvious that the practical production of such a functional unit may involve either one or more electronic circuits designed solely for the purpose of fulfilling the function described or one or more multifunctional circuits which also fulfil additional functions.

The programming console mainly comprises the matrix keyboard 20 (which was described in detail above), an ALU (arithmetic and logic unit 40), a clock 44 associated with the ALU 40 and an input and output interface 42. The parameters entered through the matrix keyboard 20 are sent to the ALU 40 where they are preconditioned before being sent via the linking interface 42 to a monitoring unit 12. After programming of an autonomous monitoring unit, the clock 44 of the ALU 40 is stopped and the ALU is put on stand-by mode. As soon as one of the keys on the keyboard 20 is pressed, a NOR gate 46 generates a signal that restarts the clock 44 and reactivates the ALU 40. This mode of operation economises on electrical power.

2) The autonomous monitoring units.

Figure 3:
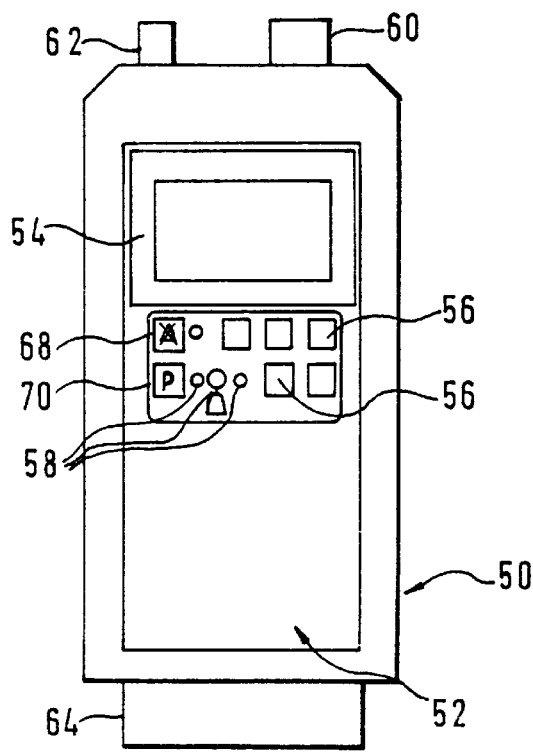
FIG. 3 represents a view of an autonomous monitoring unit.

Reference is first made to FIG. 3, showing the general external appearance of an autonomous monitoring unit 12 according to the invention. The autonomous monitoring unit 12 is incorporated into a case 50, preferably a hermetically sealed case to facilitate the sterilisation of the unit. On its front surface 52, the case 50 is equipped with an LCD display screen 54, with various control buttons 56 and with indicator lamps 58.

This case 50 also has a input terminal 60 to connect it to the connecting cable from the sensor 14 and an optical window 62 to connect it to the optical coupler 15, which is connected electrically to the programming console (see FIG. 1). It will be noted that the case 50 does not include any means for inputting infusion parameters. This is because each autonomous monitoring unit 12 is programmed for a given infusion and is allocated to this for its whole duration. A change of programmed parameters is not in principle required and should be made, if necessary, by connecting the autonomous monitoring unit 12 once again to the programming console.

The reference number 64 denotes a storage battery which is connected in the case in such a way that it can be changed while the device is running. A stand-by electric cell or storage battery, incorporated in the unit itself, provides a power supply during the exchange of an exhausted storage battery 64 so that there is no interruption of the monitoring. Alternatively or in addition, the case may also be provided with connectors for an external battery in such a way that a storage battery 64 can be removed without causing an interruption in the electrical power supply. A warning signal precedes the complete exhaustion of the interchangeable battery for a duration of about thirty minutes.

Integrated inside the case 50 is an audible alarm unit. A button 68 enables the audible alarm to be stopped, but the alarm is automatically restarted if the detected fault persists.

A key denoted by the reference number 70 enables the monitoring to be suspended for a fixed time in order to allow intervention with the infusion.

Figure 5:
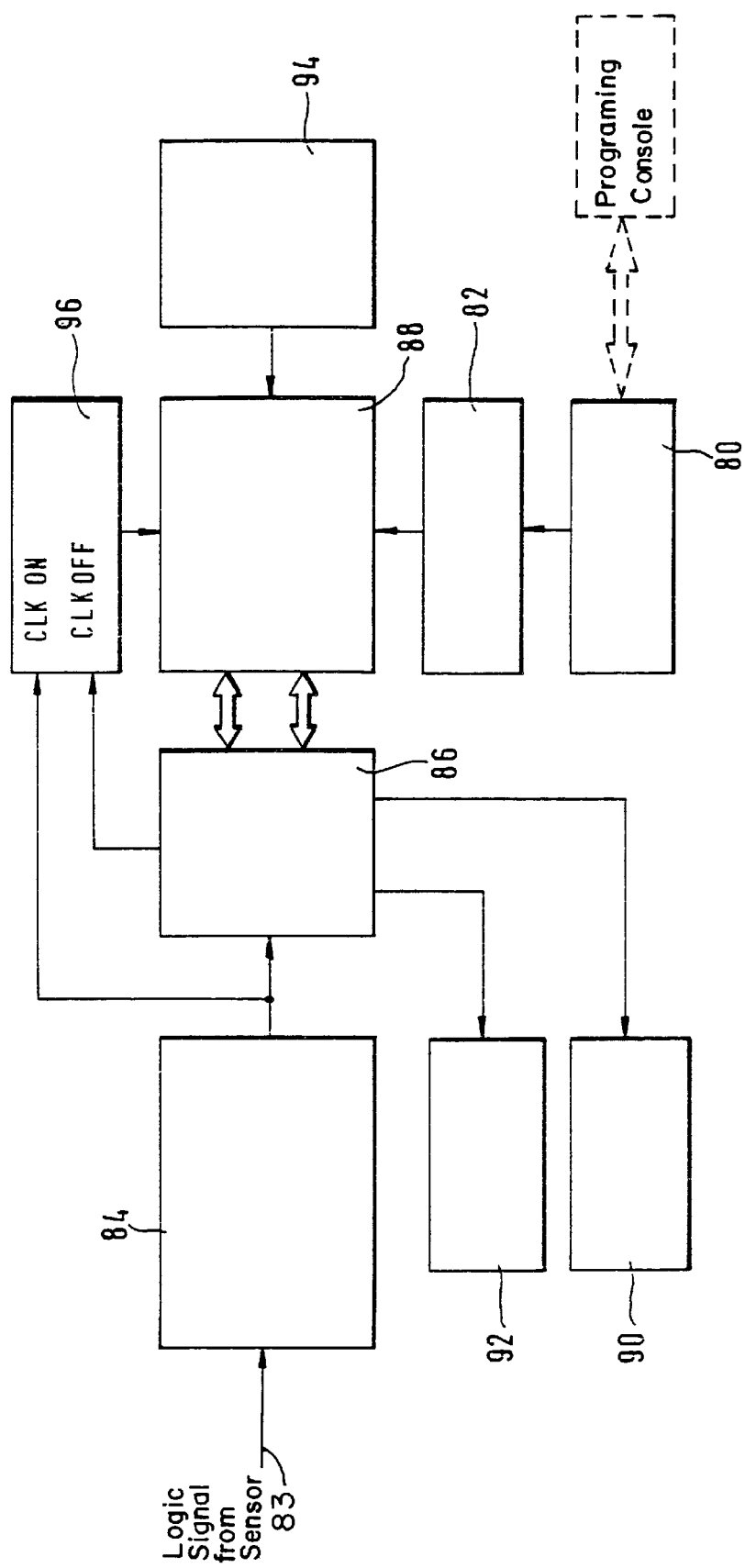
FIG. 5 is a functional block diagram of an autonomous monitoring unit.

The functioning and the internal structure of the autonomous monitoring unit will be described briefly with the help of FIG. 5. Each rectangle represents a different functional unit. It is obvious that the practical production of such a functional unit may involve either one or more electronic circuits designed solely for the purpose of fulfilling the function described or one or more multifunctional circuits which also fulfil additional functions.

The infusion parameters are entered through a parametric input interface 80 forming part of the optical window 62. These infusion parameters are stored in a memory unit 82 which is connected to an arithmetic and logic unit 88. The input interface 80 sends to the programming console 10 a reception protocol.

A logic signal 83 from the drip sensor 14 is received by a timer-counter unit 84. This latter unit measures the time interval between two drops, or provides a signal that a period of time has elapsed with no drops being detected which exceeds some limiting period of time. When a drop does pass, a specific signal is triggered. Through the input/output ports 86, the ALU 88 is therefore informed of the time separating two drops or of the excessive delay in the appearance of a drop.

A computer algorithm, handled by the ALU 88, compares the data received from the timer-counter unit 84 with the values stored in the memory unit 82 and sets off an audible and/or visual alarm on an alarm unit 90, for example if the measured time interval between several successive drops exceeds the preprogrammed margins of tolerance. The ALU 88 also controls a display unit 92, providing for the display of the measured parameters and the programmed parameters.

The reference number 96 denotes a high-frequency oscillator synchronising the ALU 88. Between successive events (passage of a drop, exceeding of the limiting time between two drops or fault in the sensor), once the data processing has finished, the electrical power consumption in the monitoring unit is reduced through the ALU 88 being inactivated by the stoppage of the oscillator 96.

In order to facilitate an initial adjustment of the infusion flow rate, the autonomous monitoring unit is preferably provided in addition with a switching circuit 94 in order to switch from a "monitoring/alarm" functioning mode to a "flow rate adjustment" functioning mode. In this latter functioning mode, the audible alarms are out of action and a sound unit advantageously produces an acoustic signal for each drop detected. The nurse thus has available an efficient instrument, completely preprogrammed, to carry out the initial adjustment of an infusion by gravity. Calculations of the number of drops and the manual timing of drops are no longer required. As a result, it is impossible to make a mistake over the adjustment of the flow rate.

Figure 6:
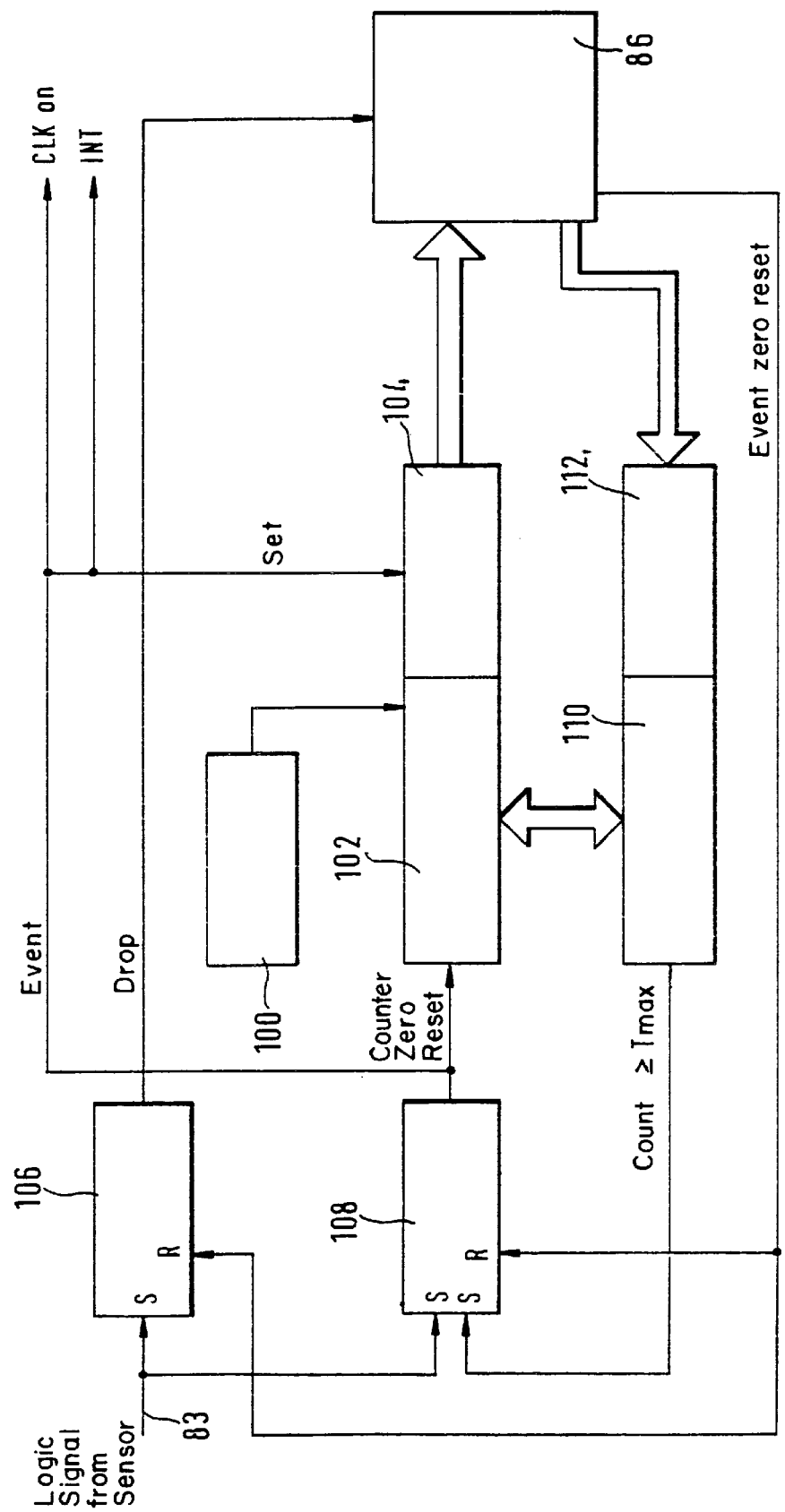
FIG. 6 is a functional block diagram of a timing and counting unit of an autonomous monitoring unit.

The unit for timing and counting drops is described by reference to FIG. 6.

Pulses from a low frequency clock 100 are counted down by counter-divider circuits 102. For a frequency of 512 Hz, 16-bit counting allows for a time of more than a minute between two drops, which is equivalent to about three to four times the limiting time for a very low flow rate (250 ml in 24 hours). The value from the counter-divider circuits 102 is at the same time passed to data-latch circuits 104.

The logic signal 83 from the sensor 14 indicating the passage of a drop causes a low-to-high transition at the output of the two set/reset latches 106 and 108. The transition of 106 indicates to the ALU 88 that there was passage of a drop, while the transition 108 indicates merely that there has been an event (passage of a drop, exceeding of the limiting time between two drops or fault in the sensor). The signal of an event restarts the oscillator 96 of the ALU, causing an interruption of the ALU 88. In parallel with this, the signal of an event fixes the counting down of pulses on the data-latch circuits 104 and resets the pulse counters 102 to zero. The value of the counters 102 preserved on the data-latch circuits 104 serves to determine the time that has elapsed since the last drop signal. In the presence of the drop signal supplied by the set/reset latch 106, this value can be accumulated by the ALU 88 on a four-byte variable (26 data bits for 24 hours), which allows the total time elapsed since the beginning to be measured without the need for an additional time counter. The number of drops that has passed can be accumulated on a two-byte variable (15 data bits for a volume of 1600 ml). After these data have been processed by the ALU, the latter resets the set/reset latches 106 and 108 to zero, which also restarts the counting down of pulses on the data-latch circuits 104. The ALU 88 is then put into the stand-by state at low power consumption by the stoppage of its oscillator 96.

In the absence of a drop signal at the sensor, a comparator 110 constantly compares the values on the counters 102 with a limiting time interval between two drops. The latter, which is stored in a register 112 of the memory unit 82, has been fixed by the programming of the monitoring unit in terms of the volume and the duration of the infusion. If the value on the counters 102 exceeds this limiting time, the comparator 110 causes a low-to-high transition at the output of the set/reset latch 108 without causing a transition at the output of the set/reset latch 106. This logic status will be interpreted by the algorithm of the ALU 88 as a situation requiring the triggering of an alarm.

The computer algorithm of the autonomous monitoring unit is with advantage designed to trigger different levels of alarm, for example:

absence of a drop signal during a time interval greater than an authorised time interval (fixed for example by taking into account a calculated mean interval and a given extreme relative deviation); this may correspond either to an absence of any flow or to a continuous flow through the drip orifice: absolute priority alarm.

flow rate outside fixed limits for several consecutive drops: warning by a brief signal during the detection of the drop.

instantaneous flow rate outside extreme limits (e.g.: absolute deviation greater than 25%) between two drops: warning.

instantaneous flow rate outside extreme limits over several consecutive drops: continuous alarm.

momentary stoppage by the operator (e.g. for intervention in the infusion or for patient care): indication by a specific signal at a fixed time interval of the stand-by state of the monitoring unit, and indication of the passage of each drop.

run-down battery: priority alarm capable of being momentarily de-activated, for a period corresponding to a fraction of the reserve time (internal stand-by battery), followed by an alarm that cannot be de-activated when there is a fault in replacing the battery.

The computer algorithm also makes it possible to calculate the following indicative data giving continuous information about the state of the infusion:

Fraction of the total volume infused: this is the ratio of the number of drops that has already passed to the number of drops in the total volume to be infused; this gives an indication of the progress of the infusion more precise than the graduations on the receptacles (preferably displayed as a %).

Optimum flow rate to maintain the total time equal to the initially planned time: this is the difference between the number of drops corresponding to the total volume of the infusion and the total number of drops that has already passed, divided by the difference between the planned total duration and the time elapsed since the beginning (preferably displayed as a relative %).

Instantaneous flow rate: this is a quantity inversely proportional to the time between two consecutive drops.

Mean flow rate: this is the ratio between the number of drops infused and the time that has elapsed since the beginning.

Figure 9:
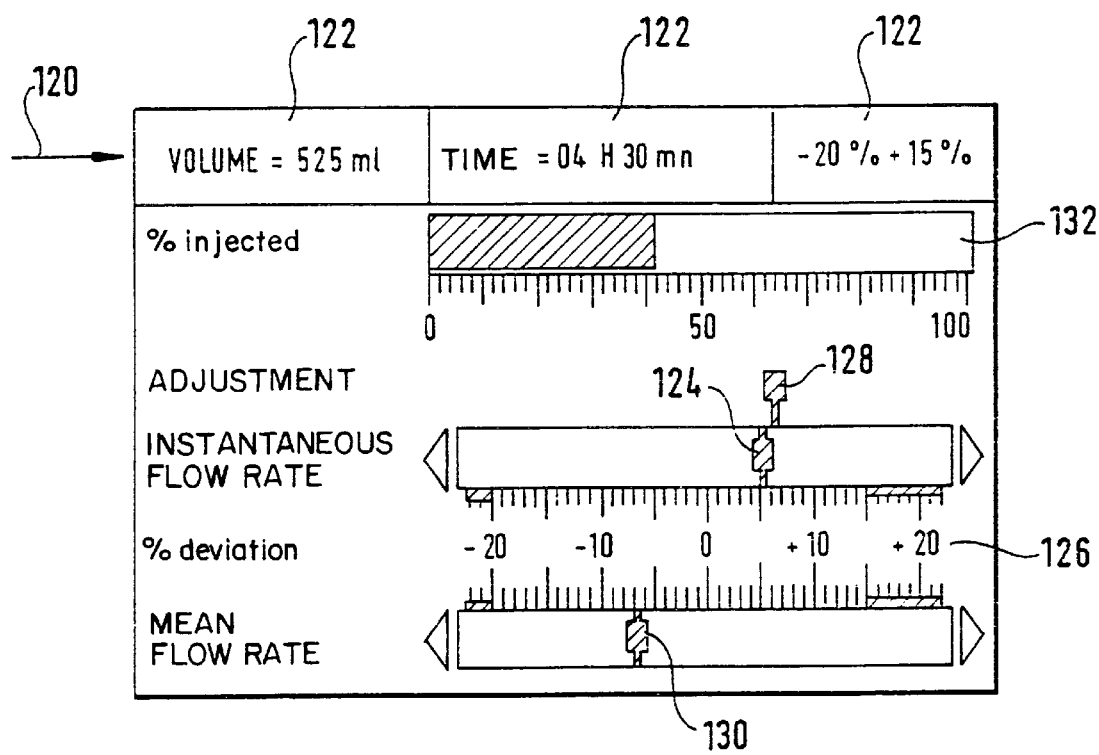
FIG. 9 shows a configuration of a display screen of an autonomous monitoring unit.

FIG. 9 represents a preferred method of displaying these indications. At the very top of the display there is a status line 120 indicating the pre-programmed parameters of the infusion 122. Below that, a first graphics cursor 124, pseudo-analogue, moves over a scale 126 graduated in percentage deviations compared with the ideal values entered initially or calculated, and represents a moving mean of the flow rate (this moving mean is for example calculated over the last eight drops). A second moving cursor 128 represents the optimum flow rate calculated in order to respect the initially planned duration for the infusion. A third cursor 130 indicates the mean flow rate since the beginning of the infusion. Lastly, a third display 132 shows the fraction of the total volume infused.

An autonomous monitoring unit 12 may also comprise, as additional equipment, a transmitter or transceiver which sends either data and/or alarms to a monitoring station (if necessary, possibly through the intermediary of a relay repeater). The transceiver allows a remote interrogation of each autonomous monitoring unit by sending a coded identification sequence corresponding to the autonomous monitoring unit that is to be interrogated. Remote monitoring of all the indicators of the progress of the infusion is then possible.

3) The drip sensor

Figure 4:
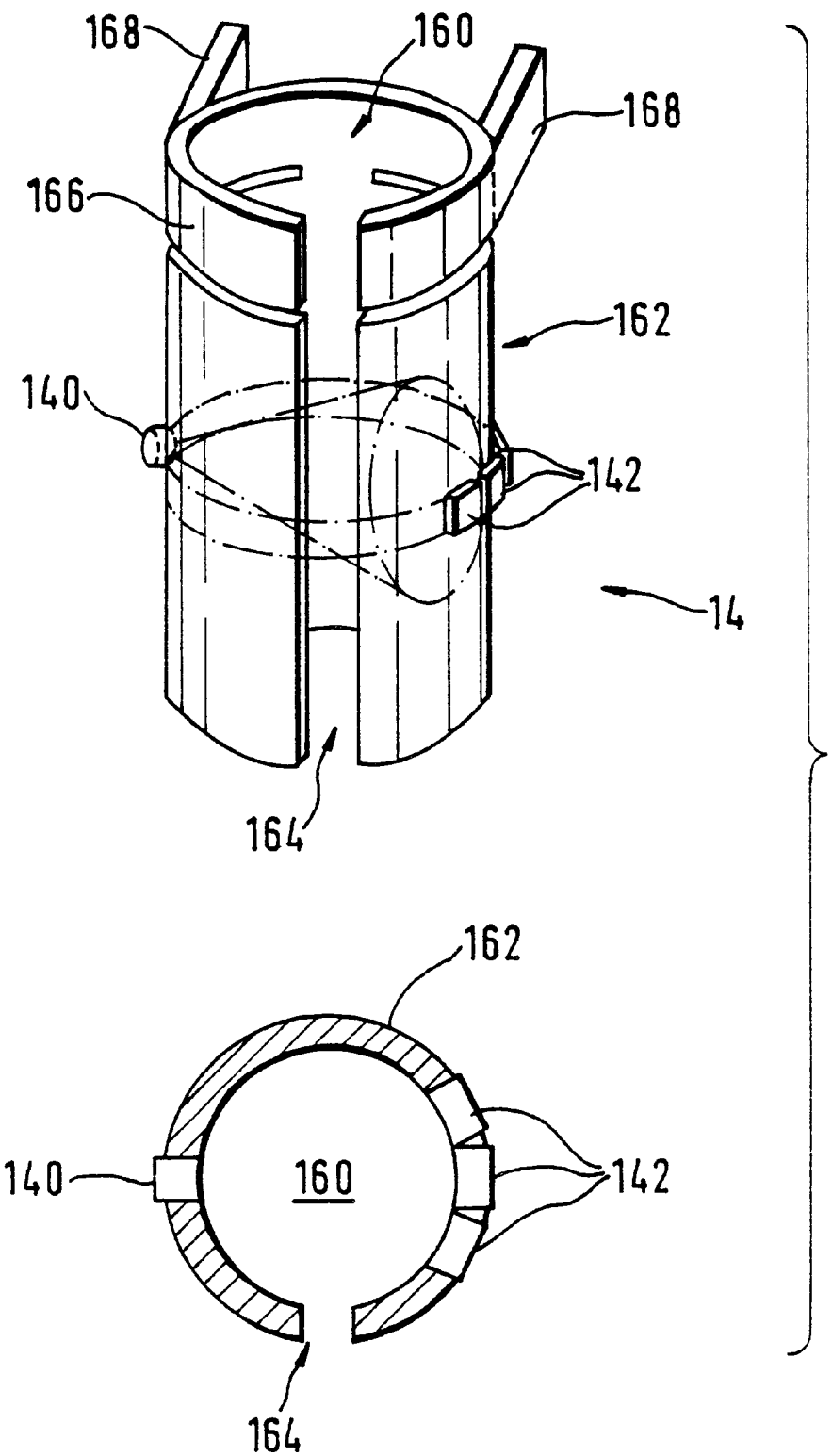
FIG. 4 represents a view of the drip sensor.
Figure 8:
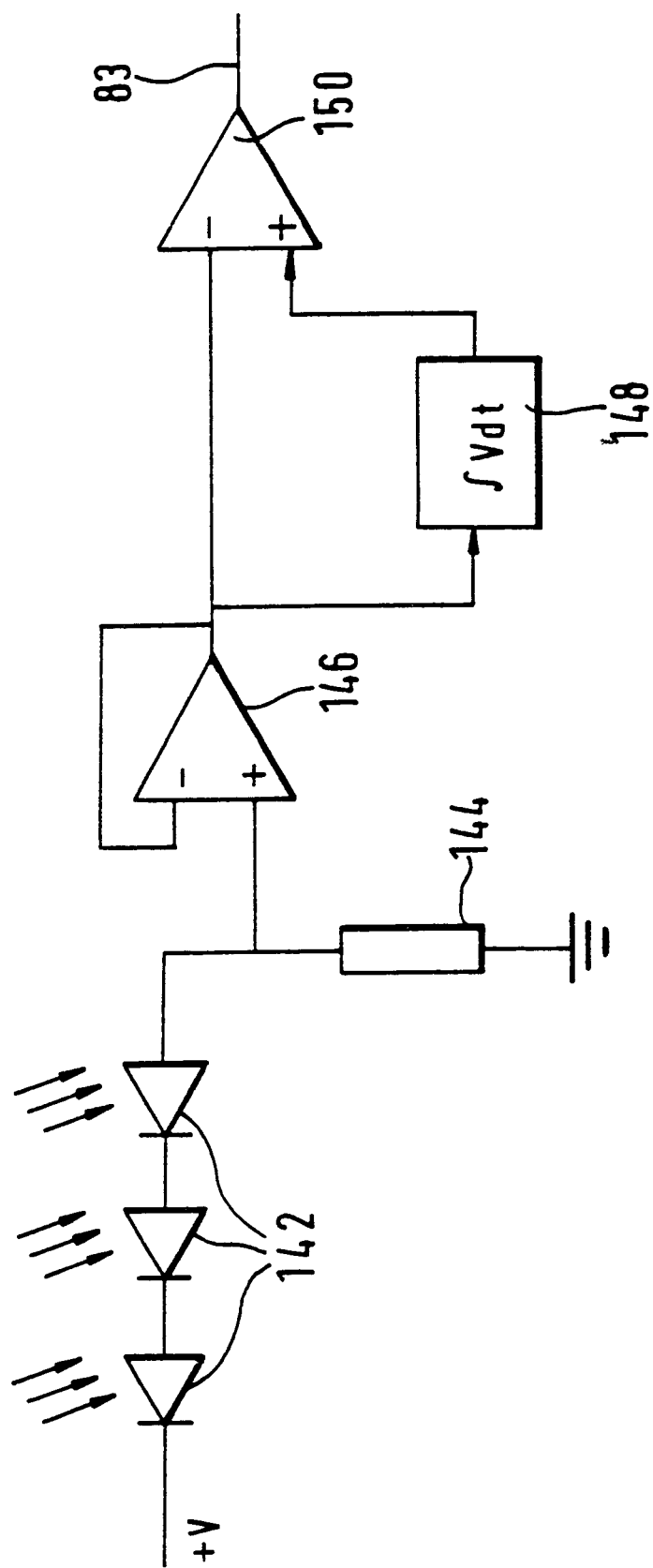
FIG. 8 is a functional block diagram of a drip sensor.

For the description of the sensor, reference is made to FIGS. 4 and 8. The sensor 14 connected to an autonomous monitoring unit 12 is an electro-optical sensor of the optical barrier type, using a source 140 and a receiver 142 preferably working in the near infra-red (800 to 950 nanometres). This spectral range in fact has particular technical advantages such as: short response times of emitters and detectors; absence of memory effects in receivers; low sensitivity to stray light.

The emitter 140 and the receiver 142 operate in pulsed synchronous mode, which has the following main advantages:

great insensitivity to stray light (50 Hz or 60 Hz), which is very intense in this spectral range when high-temperature thermal light sources of the incandescent halogen lamp type are used;

high sensitivity combined with a low power consumption, the emission occurring at fixed intervals for a very short time (low cyclic ratio); in other words, the peaks of emission from the transmitter may be very powerful while the mean consumption remains low.

It should be appreciated that the proposed sensor is designed to detect not only drops passing into a region near the central axis of the drip cylinder, but also those passing at a distance from this axis, for example when the cylinder is inclined or suffers vibrations or is knocked. For this purpose, the receiver comprises several photodiodes 142 (three photodiodes, for example) positioned in an angular sector opposite the source 140. Each of these photodiodes is in a position to limit a current passing through a bias resistor 144 placed in the input of an impedance matching amplifier 146 in case it receives a reduced amount of light during the passage of a drop. Unlike systems with a narrow beam, where the drop has to intercept a large proportion of the light beam in order to trigger the detection signal, only a moderate variation in the overall flux is necessary here to detect a drop. The signal from the impedance matching amplifier 146 is then integrated by an integrating amplifier 148 in order to provide a mean value, amplified by an adjustable factor. A comparator 150 compares this mean value with the non-integrated signal and thus provides the logic signal 83 from the sensor 14.

The drip cylinder is with advantage introduced into a cylindrical measuring channel 160 cut into a supporting block 162. This measuring channel 160 preferably has an internal reflecting surface at the level of the optical barrier in order to produce multiple reflections of the light emitted by the source. The photodiodes 142 of the receiver then detect the perturbation produced by the passage of the drop in this system of multiple reflections inside the measuring channel 160. It will be appreciated that, with this proposed detection system, it is almost impossible to miss a drop.

It can be seen in FIG. 4 that the measuring channel 160 is accessible through a lateral slit 164 cut into the supporting block 162 along a generator of the cylindrical channel. This slit 164 has a width allowing the passage of a flexible tube conveying the liquid from the ampoule towards the infusion catheter (a tube generally called "tubing"). This enables the drip cylinder to be introduced easily into the measuring channel. The upper part 166 of this supporting block 162 preferably comprises two flexible branches which can be moved apart and which, when released, tighten themselves around the upper part of the ampoule to keep it in place. Two levers 168, positioned on opposite sides of the slit, then enable the two branches to be moved apart when they are squeezed in order to position the supporting block over the ampoule. The optical and electronic components are positioned laterally, for example in one or two cabinets adjoining the supporting block 162.

I claim:

1. A device for monitoring an infusion, comprising:
    a sensor adapted for being combined with a drip cylinder to detect the presence or absence of a drop; and
    a timing and counting unit timing and counting for the drops detected by said sensor; said sensor comprising:
    a) a source of infa-red radiation, said source of infrared radiation functioning in pulsed mode, and
    b) an optical receiver, said optical receiver being activated synchronous to said source of infra-red radiation;
    c) an integrating amplifier adapted for integrating the signal from said optical receiver and for providing as an output signal a mean value amplified by an adjustable factor; and
    d) a comparator adapted for comparing said output signal with the non-integrated signal from said receiver and for generating a logic signal as an input signal for said timing and counting unit.

2. A device as claimed in claim 1, wherein said optical receiver comprises several photodiodes, said photodiodes being electrically connected in series and being distributed in an angular sector opposite said source of infra-red radiation.

3. A device for monitoring an infusion, comprising:
    a) a sensor adapted for being combined with a drip cylinder to detect the presence or absence of a drop;
    b) monitoring means connected to said sensor associated with said drip cylinder during the infusion; said monitoring means comprising:
        a memory unit for storing characteristic parameters of said infusion;
        a unit for timing and counting the drops detected by said sensor and for generating a first signal indicative thereof;
        a display unit;
        an acoustic and/or visual alarm unit;
        a first arithmetic and logic unit adapted for using a computer algorithm, said computer algorithm incorporating as parameters said signal from said timing and counting unit and said characteristic parameters of the infusion stored in said memory unit, in order to trigger said acoustic and/or visual alarm; and
        an autonomous source of electrical power for supplying said memory unit, said timing and counting unit, said display unit, said acoustic and/or visual alarm unit and said first arithmetic and logic unit;
    said memory unit, said timing and counting unit, said display unit, said acoustic and/or visual alarm unit, said first arithmetic and logic unit and said autonomous source of electrical power being integrated into a first housing so as to form an autonomous and independent unit;
    c) an autonomous and independent programming console, said programming console comprising:
        a data input unit adapted for entering characteristic parameters of said infusion;
        a second arithmetic and logic unit, said second arithmetic and logic unit being adapted for preconditioning said characteristic parameters of said infusion entered into said data input unit; and
        an output interface, said output interface being adapted for converting said preconditioned parameters into signals capable of being transmitted to said monitoring means;
    said monitoring means further comprising an input interface adapted for reconstituting said preconditioned parameters from said signals generated by the said output interface of said programming console, so that said preconditioned parameters can be loaded into said memory unit of said monitoring means by temporarily coupling said input interface of said autonomous and independent monitoring unit to said output interface of said autonomous and independent programming console.

4. A device as claimed in claim 3, wherein said first arithmetic and logic unit includes an oscillator and said monitoring means further comprise means for inactivating said first arithmetic and logic unit by stoppage of its oscillator between two successive events, where an event is classed as the passage of a drop, the exceeding of the limiting time between two drops or a fault in the sensor.

5. A device as claimed in claim 4, wherein said timing and counting unit comprises
    a) first logic means, said first logic means generating a transition of a first logic signal when an event of the first type occurs, said event of the first type corresponding either to the passage of a drop, to the exceeding of the limiting time between two drops or to a fault in the sensor, said first logic means restarting the oscillator of said first arithmetic and logic unit during an event of the first type;
    b) second logic means, said second logic means generating a transition of a second logic signal solely during the passage of a drop, said second logic means triggering the execution of a computer algorithm during the passage of a drop in said first arithmetic and logic unit;
    c) wherein an alarm is generated when there is a transition of said first logic signal and no transition of said second logic signal.

6. A device as claimed in claim 5, wherein said timing and counting unit further comprises:
   a) a pulse counter for counting the pulses from a low frequency clock;
   B) a data-latch circuit, said data-latch circuit being associated with said pulse counter and being connected to said first arithmetic and logic unit so that it can be interrogated by the latter;
   said first logic means being connected to said pulse counter and to said data-latch circuit so as to freeze the counting down of the pulses in said data-latch circuit and to reset the pulse counters to zero during a transition of said first logic signal.

7. A device as claimed in claim 6, wherein said timing and counting unit further comprises a comparator constantly comparing the value on the pulse counter with a predetermined limiting time interval, said comparator causing a transition of said first logic signal when said predetermined limiting time interval is exceeded.

8. A device as claimed in claim 3, wherein said sensor comprises
   a) a source of infra-red radiation, said source of infrared radiation functioning in pulsed mode, and
   b) an optical receiver, said optical receiver being activated synchronous to said source of infra-red radiation.

9. A device as claimed in claim 8, wherein said optical receiver comprises several photodiodes, said photodiodes being electrically connected in series and being distributed in an angular sector opposite said source of infra-red radiation.

10. A device as claimed in claim 8, wherein said sensor further comprises:
    a) an integrating amplifier adapted for integrating the signal from said optical receiver and for providing as an output signal a mean value amplified by an adjustable factor; and
    b) a comparator adapted for comparing said output signal with the non-integrated signal from said receiver and for generating a logic signal as an input signal for the timing and counting unit.

11. A device as claimed in claim 3, wherein said first arithmetic and logic unit is adapted for continuously calculating an optimum number of drops, said optimum number of drops being displayed on said linear scale in the form of a cursor indicating the relative deviation of the said optimum number of drops from the number corresponding to zero deviation, defined as follows:

$$\frac{\left(\left(\sum \text{drops yet to pass}\right) - \left(\sum \text{drops already passed}\right)\right) * (\text{duration } t1 \text{ of the observation interval})}{(\text{planned total duration of infusion}) - (\text{duration already elapsed})}$$

12. A device as claimed in claim 3, wherein said data input unit comprises means for
    entering a margin of tolerance applicable to the number of drops detected in a time interval, said margin of tolerance being incorporated in said computer algorithm in order to delay the triggering of an alarm.

13. A device as claimed in claim 12, wherein said means for entering a margin of tolerance for the infusion flow rate comprise
    means for entering a first margin of tolerance applicable to the number of drops detected in a time interval in the case where this number is less than a mean value calculated for the same time interval; and
    means for entering a second margin of tolerance applicable to the number of drops detected in a time interval in the case where this number is greater than a mean value calculated for the same time interval.

14. A device as claimed in claim 3, wherein said display unit comprises means for displaying said characteristic parameters of the infusion, said characteristic parameters being deduced from the parameters loaded into said memory unit of said monitoring means.

15. A device as claimed in claim 14, wherein said displayed characteristic parameters comprise the volume of the infusion, the duration of the infusion and the margins of tolerance.

16. A device as claimed in claim 3, wherein said display unit comprises means for displaying graphically on a linear scale the positive or negative difference between the number of drops detected during an interval of observation t1 and the number of drops there should have been during the said interval t1 in the case of a uniform distribution of drops over the total duration initially planned for the infusion.

17. A device as claimed in claim 16, wherein said first arithmetic and logic unit is adapted for continuously calculating an optimum number of drops, said optimum number of drops being displayed on said linear scale in the form of a cursor indicating the relative deviation of the said optimum number of drops from the number corresponding to zero deviation, defined as follows:

$$\frac{\left(\left(\sum \text{drops yet to pass}\right) - \left(\sum \text{drops already passed}\right)\right) * (\text{duration } t1 \text{ of the observation interval})}{(\text{planned total duration of infusion}) - (\text{duration already elapsed})}$$

18. A device as claimed in claim 3, wherein said data input unit comprises means for entering a volume of the infusion and means for entering a duration of the infusion.

19. A device as claimed in claim 3, wherein said data input unit further comprises means for entering parameters used in calibration.

20. A device as claimed in claim 3, wherein said data input unit comprises a keyboard, each key of said keyboard being dedicated to a precise value of a characteristic parameter of the infusion.

21. A device as claimed in claim 3, further comprising optical coupler, said optical coupler being adapted for temporarily coupling said input interface of said monitoring means to said output interface of said programming console.

22. A device as claimed in claim 3, wherein said monitoring means further comprise:
    a) switching means for switching between a monitoring/alarm mode and an adjustment mode, said adjustment mode being used for adjusting the flow rate of said infusion, said acoustic alarms being out of action in said adjustment mode; and
    b) an acoustic unit capable of producing an acoustic signal for each drop detected in said "adjustment of flow rate" mode.

23. A device for monitoring an infusion, comprising:
    a) a sensor adapted for being combined with a drip cylinder to detect the presence or absence of a drop;
    b) monitoring means connected to said sensor associated with said drip cylinder during the infusion; said monitoring means comprising:

a memory unit for storing characteristic parameters of said infusion;

a unit for timing and counting the drops detected by said sensor and for generating a first signal indicative thereof;

a display unit, wherein said display unit comprises means for displaying graphically on a linear scale the positive or negative difference between the number of drops detected during an interval of observation t1 and the number of drops there should have been during the said interval t1 in the case of a uniform distribution of drops over the total duration initially planned for the infusion;

an acoustic and/or visual alarm unit;

a first arithmetic and logic unit adapted for using a computer algorithm, said computer algorithm incorporating as parameters said signal from said timing and counting unit and said characteristic parameters of the infusion stored in said memory unit, in order to trigger said acoustic and/or visual alarm.

* * * * *